(12) United States Patent
Van Putten (10) Patent No.: US 9,089,383 B2
(45) Date of Patent: Jul. 28, 2015

(54) DENTAL SHAPING STRIP

(71) Applicant: Clifford John Van Putten, Hudsonville, MI (US)

(72) Inventor: Clifford John Van Putten, Hudsonville, MI (US)

( * ) Notice: Subject to any disclaimer, the term of this patent is extended or adjusted under 35 U.S.C. 154(b) by 0 days.

(21) Appl. No.: 14/148,636

(22) Filed: Jan. 6, 2014

(65) Prior Publication Data

US 2014/0220507 A1    Aug. 7, 2014

Related U.S. Application Data

(63) Continuation-in-part of application No. 13/757,471, filed on Feb. 1, 2013.

(51) Int. Cl.
  *A61C 3/06* (2006.01)
  *A61C 3/12* (2006.01)
  *A61C 15/04* (2006.01)

(52) U.S. Cl.
  CPC ... *A61C 3/06* (2013.01); *A61C 3/12* (2013.01); *A61C 15/04* (2013.01)

(58) Field of Classification Search
  CPC .......... A61C 3/06; A61C 15/00; A61C 15/04; A61C 15/041; A61C 5/04; A61C 5/125; A61C 5/127; A61C 17/00; A61C 3/12
  USPC ......... 433/142, 39, 42, 43; 132/321, 323, 329
  See application file for complete search history.

(56) References Cited

U.S. PATENT DOCUMENTS

| | | | |
|---|---|---|---|
| 217,300 A | 7/1879 | Starr | |
| 522,211 A | 7/1894 | Saupe | |
| 3,108,377 A * | 10/1963 | Meyer | 433/39 |
| 3,145,472 A * | 8/1964 | Tofflemire | 433/39 |
| 3,779,256 A * | 12/1973 | Maloney et al. | 132/329 |
| 3,795,052 A * | 3/1974 | Mowery | 433/39 |
| 3,842,505 A * | 10/1974 | Eames | 433/39 |
| 4,187,082 A | 2/1980 | Guerra | |
| 4,270,902 A | 6/1981 | Wiland | |
| 4,373,915 A * | 2/1983 | Comstock | 433/136 |
| 4,563,152 A * | 1/1986 | McClure | 433/39 |

(Continued)

FOREIGN PATENT DOCUMENTS

WO   WO 2006056989 A1 *   6/2006   ............... A61C 5/12

OTHER PUBLICATIONS

International Search Report of corresponding PCT Application No. PCT/US2014/013760 dated May 9, 2014.

*Primary Examiner* — Robyn Doan
*Assistant Examiner* — Tatiana Nobrega
(74) *Attorney, Agent, or Firm* — Global IP Counselors (57) ABSTRACT

A dental shaping strip includes a base portion and a shaping portion. The base portion has a first base surface and a second base surface facing in an opposite direction from the first base surface. The first and second base surfaces have prescribed longitudinal lengths and prescribed widths transverse to the prescribed longitudinal lengths. The shaping portion is connected to a longitudinal edge of the base portion. The shaping portion has a first shaping surface connected to the first base surface, with at least part of the first shaping surface being abrasive. The first and second base surfaces are at least partially non-abrasive. Preferably, the first shaping surface and the first base surface diverge from each other as they approach longitudinal free edges of the dental shaping strip. Preferably, the first and second base surfaces are non-abrasive along their prescribed longitudinal lengths.

10 Claims, 9 Drawing Sheets

(56) References Cited

U.S. PATENT DOCUMENTS

| | | | |
|---|---|---|---|
| 4,690,642 A | 9/1987 | Kyotani | |
| 5,425,635 A * | 6/1995 | Croll | 433/39 |
| 5,476,381 A | 12/1995 | Dragan | |
| 5,507,646 A * | 4/1996 | Roth | 433/216 |
| 6,234,793 B1 * | 5/2001 | Brattesani et al. | 433/39 |
| 6,619,956 B1 * | 9/2003 | Weir | 433/39 |
| 6,712,608 B2 * | 3/2004 | Bills | 433/39 |
| 7,537,450 B2 | 5/2009 | Karazivan | |
| 7,914,284 B2 | 3/2011 | Kim | |
| 2004/0163664 A1 | 8/2004 | Husted | |
| 2005/0089814 A1 * | 4/2005 | Slone | 433/39 |
| 2005/0244786 A1 * | 11/2005 | Freedman | 433/142 |
| 2005/0287491 A1 * | 12/2005 | Slone | 433/39 |
| 2006/0237028 A1 * | 10/2006 | Hamidy | 132/321 |
| 2007/0148613 A1 * | 6/2007 | Stoll | 433/39 |
| 2008/0064002 A1 * | 3/2008 | Clark | 433/39 |
| 2009/0220912 A1 | 9/2009 | Allen | |
| 2011/0081830 A1 | 4/2011 | Pollasky | |
| 2011/0200963 A1 | 8/2011 | Allen | |

* cited by examiner

DENTAL SHAPING STRIP

CROSS-REFERENCE TO RELATED APPLICATIONS

This application is a Continuation-In-Part application of U.S. patent application Ser. No. 13/757,471, filed on Feb. 1, 2013, pending, the entire contents of which are hereby incorporated herein by reference.

BACKGROUND

1. Field of the Invention

The present invention generally relates to a dental shaping strip. More specifically, the present invention relates to a dental shaping strip with a non-abrasive portion and an abrasive portion.

2. Background Information

Metal fillings were regularly used to fill openings in teeth, such as openings caused by tooth decay (cavities), from the $19^{th}$ century. In recent years, non-metallic materials have been used to fill openings in teeth. Currently, the most common material used to fill interproximal restorations in posterior teeth is resin based composite.

SUMMARY

It has been discovered that, despite the popularity of composite restorations, there are challenges to placing composite restorations properly. Improperly shaped restorations with sharp edges and corners will chip and fracture, resulting in premature failure. Properly placed resin based composite restorations will duplicate the embrasures, contact area, marginal ridge, and occlusal fossa of natural teeth. Composite dental restorations should mimic the smooth and rounded contours of the natural dentition to ensure longevity and oral health. The primary objective is to restore teeth to their original dimensions and natural anatomical contours. Form and function are the primary purpose of the dental apparatus and, in the final analysis of a dental restoration, the form of the restoration and its function within the dental apparatus is more important than how perfectly the restoration aesthetically matches the surrounding teeth.

The molars and premolars are the posterior teeth in the dental arch. The function of the posterior teeth is to grind food so that the food becomes small enough and soft enough to swallow. The form of the posterior teeth allows the cusps of one arch to grind into a depression or fossa of the opposing arch. There are at least three important features of the posterior teeth, (1) the contact between adjacent teeth is not at the top of the teeth but instead more toward the middle, (2) the widest part of the tooth is at the point of contact, and (3) there is space both above and below the point of contact between adjacent posterior teeth. The point of contact between the posterior teeth is referred to as the contact point or contact area. In all directions from these contact areas, the tooth surfaces diverge from each other. The spaces above and below the contact area are known as embrasures.

Occlusal to the contact area is the occlusal embrasure. The occlusal embrasure takes the shape of a "V" between adjacent posterior teeth. This "V" or occlusal embrasure does not allow food to be compacted into the contact area. As the tooth surface diverges from the contact area, toward the biting or occlusal surface, the tooth surface forms an elevated linear ridge called the marginal ridge. The marginal ridge is shaped like a hill or buttress. In unworn dentition, the height of the marginal ridge is not directly above the contact area. Instead, in unworn dentition, the height of the marginal ridge is always more toward the center of the tooth. God designed (shaped and positioned) this hill or buttress to reinforce and to impart strength to the tooth. The marginal ridge bears the forces of mastication. Although enamel generates sufficiently high compressive strength, enamel exhibits low tensile strength. Therefore, the marginal ridge is a rounded surface, with no sharp bends or corners. God has designed the marginal ridge in this manner because sharp bends and corners of enamel are prone to fracturing and chipping, e.g., due to tensile stresses that would be applied thereto. Also, the rounded surfaces of the occlusal embrasures are more self-cleansing than if the surfaces of the teeth had angles or corners where food could become entrapped.

Apical to the contact area is the gingival embrasure, which forms a triangular space. The base of the triangular space is formed by the alveolar process. The sides of the triangular space are the proximal surfaces of the adjacent teeth. The apex of the triangular space is the contact area. This triangular space is normally occupied by gingival tissue called the interdental papilla. The interdental papilla is protected from the forces of mastication by the contact area of one tooth butting tightly against the adjacent posterior tooth. If the contact area does not butt tightly against the adjacent tooth, the contact is called a light or open contact. Light or open contacts fail to protect the interdental gingival tissue from the forces of mastication, meaning that food could slip through the light or open contact area and become wedged into the interdental papilla. Food wedged into the interdental papilla is known as food impaction. Such food impaction could initiate a chain of events resulting in decay, periodontal destruction, and pain.

A current daily challenge in clinical restorative dentistry is replacing tooth tissue by placing a composite resin bonded restoration between two teeth, usually because of decay. The objectives for successfully placing a composite resin bonded restoration between two teeth include:

(A) A smooth transition from restoration to tooth is desired to prevent bacteria from accumulating causing further decay or periodontal issues. This is achieved by proper placement of modern sectional matrixes and contoured wedges being placed prior to placing the restoration. Handheld finishing strips apical or below the contact as well as fine finishing burs in a dental hand piece are used to achieve this smooth transition.

(B) Interproximal contacts that are tight, which prevent food impaction and subsequent decay and periodontal issues, are desired. The teeth are forced apart with a variety of dental springs that engage both teeth to wedge them apart to compensate for the matrix thickness.

(C) Proper occlusal contours support the opposing cusp tip in occlusion, avoiding a "high" occlusal contact point or alternatively no occlusal contacts. Proper anatomy is achieved by carefully placed uncured composite, and after being cured, by grinding the composite with finishing carbide burs and points in a dental hand piece.

(D) An anatomical occlusal embrasure is formed to prevent breakage of the marginal ridges, to minimize food impactions, and to allow insertion of dental floss.

However, currently, there is no good technique for developing the "V" shaped occlusal embrasure. Using fine needle carbide finishing burs mounted in a dental hand piece is the current technique. Unfortunately, this technique suffers from poor control, digging into the restoration and likely iatrogenic damage to the adjacent tooth.

In particular, the problem with the current technique is the shaping and smoothing of the occlusal embrasure of a composite restoration to match that of a natural tooth. The marginal ridge is a rounded surface, with no sharp bends or corners. Restorations without an occlusal fossa, marginal ridge, and occlusal embrasure result in a flat, tabletop type of restoration. Such tabletop restorations have sharp, unsupported edges that are weak and may succumb to fracture and chipping. Resin composite materials have low fracture toughness in comparison to metallic restorations. Sharp angles or corners that are incorporated into an interproximal restoration also present a greater oral hygiene challenge for the patient, as sharp edges can snag and shred floss. Therefore, ideally a fossa, marginal ridge and occlusal embrasure should be formed prior to photo activation of the composite resin restoration material. However, clinically (in practice) it is a very difficult task to form a fossa, marginal ridge and occlusal embrasure prior to photo activation. Accordingly, it is necessary to shape the composite restoration after photo activation (curing). Currently, the only technology to shape this area subsequent to curing a composite restoration is with rotary instruments. However, using rotary instruments after curing results in the problem of digging into or damaging both the new restoration and the adjacent tooth as mentioned above.

Figures 19, 20:
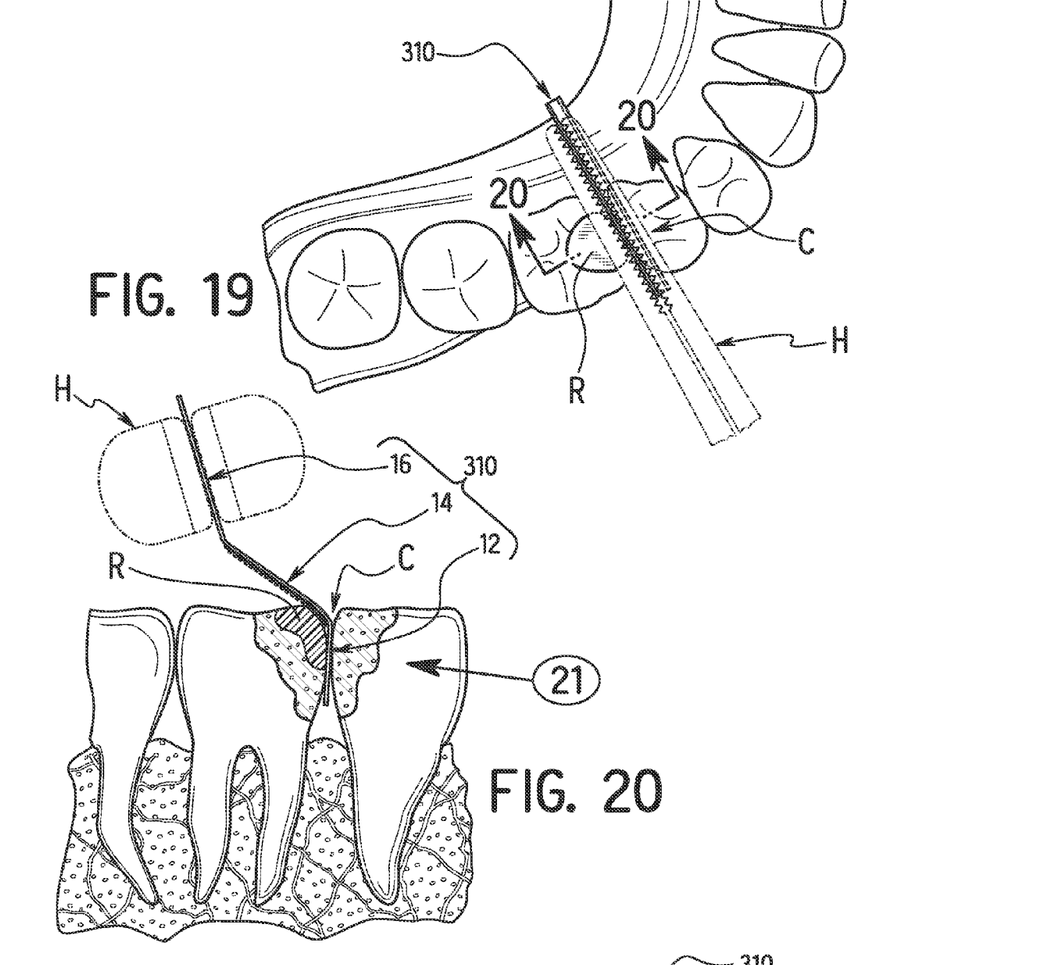
FIG. 19 is a top view of a dental shaping strip in accordance with a third embodiment being used on an interproximal restoration of a posterior tooth of the lower dentition.
FIG. 20 is a cross-sectional view the dental shaping strip being used on the interproximal restoration of the posterior lower tooth illustrated in FIG. 19, as seen along section line 20-20 of FIG. 19.

While many devices have been designed or created to shape and smooth the interproximal surface or the contact area, none of these devices meets the need for shaping the occlusal embrasure area. These devices are generally referred to as finishing strips. Finishing strips are typically thin strips of Mylar plastic or stainless steel, which is smooth (safe) on one side and has abrasive applied to the other side. The key feature is the abrasive side is slid back and forth below the contact area in the gingival embrasure (FIG. 19 and FIG. 20), and along the surface the tooth, smoothing the restoration. If the finishing strip is inserted between the contacts great care must be exercised because any reduction by finishing diminishes the contact's tightness. Attempting to shape and smooth the occlusal embrasure area using conventional finishing strips results in a reduction of the tightness of the interproximal contact and likely an open contact between the teeth.

Accordingly, one object of the present disclosure is to provide a dental shaping strip that will not abrade adjacent teeth when it is inserted between their contacts.

Another object of the present disclosure is to provide a dental shaping strip that abuts the contact area of the newly placed composite restoration without diminishing the contact area's tightness.

Another object of the present disclosure is to provide a dental shaping strip that makes it possible to shape the occlusal embrasure at an interproximal composite dental restoration so as to become shaped in the desired "V" shape, but without digging into or damaging both the new restoration and the adjacent tooth.

Yet another object of the present disclosure is to provide a dental shaping strip that makes it possible to shape the composite dental restoration to match a shape of a natural tooth (e.g., to have a rounded marginal ridge), i.e., without sharp bends or corners and without a tabletop structure.

In view of the state of the known technology a dental shaping strip is provided that basically includes a base portion and a shaping portion. The base portion has a first base surface and a second base surface facing in an opposite direction from the first base surface. The first and second base surfaces have prescribed longitudinal lengths and prescribed widths transverse to the prescribed longitudinal lengths. The shaping portion is connected to a longitudinal edge of the base portion. The shaping portion has a first shaping surface connected to the first base surface, with at least part of the first shaping surface being abrasive. The first and second base surfaces are at least partially non-abrasive. The first shaping surface and the first base surface diverge from each other as the first base surface and the first shaping surface approach longitudinal free edges of the dental shaping strip.

In view of the state of the known technology a dental shaping strip is provided that basically includes a base portion and a shaping portion. The base portion has a first base surface and a second base surface facing in an opposite direction from the first base surface. The first and second base surfaces have prescribed longitudinal lengths and prescribed widths transverse to the prescribed longitudinal lengths. The shaping portion is connected to a longitudinal edge of the base portion. The shaping portion has a first shaping surface connected to the first base surface, with at least part of the first shaping surface being abrasive. The first and second base surfaces of the base portion are non-abrasive along the prescribed longitudinal lengths thereof.

Other objects, features, aspects and advantages of the disclosed dental shaping strip will become apparent to those skilled in the art from the following detailed description, which, taken in conjunction with the annexed drawings, discloses preferred embodiments of the dental shaping strip.

BRIEF DESCRIPTION OF THE DRAWINGS

Referring now to the attached drawings which form a part of this original disclosure.

DETAILED DESCRIPTION OF EMBODIMENTS

Selected embodiments will now be explained with reference to the drawings. It will be apparent to those skilled in the art from this disclosure that the following descriptions of the embodiments are provided for illustration only and not for the purpose of limiting the invention as defined by the appended claims and their equivalents.

Referring initially to FIGS. 1-5, a dental shaping strip 10 is illustrated in accordance with a first embodiment. The dental shaping strip 10 is a hand held, flexible, thin, metal or plastic strip including a base portion 12 and a shaping portion 114.

The base portion 12 is preferably non-abrasive on both sides. The base portion 12 is sized to be received in the interproximal contact area C between adjacent posterior teeth. Because the base portion 12 is non-abrasive on both sides, the adjacent posterior teeth will not be abraded by the base portion 12 when the base portion is disposed in the contact area C. Thus, when used in the presence of a newly placed interproximal composite restoration R, the contact's tightness will not be diminished.

The shaping portion 14 is preferably abrasive in order to shape the interproximal restoration R. In particular, the shaping portion 14 is configured to facilitate shaping the interproximal restoration R so that the occlusal embrasures take the desired "V" shape (i.e., match the occlusal embrasures of natural teeth) despite the presence of the interproximal restoration, and without digging into or damaging both the new restoration R and the adjacent tooth, as seen FIG. 3 for example. In addition, the shaping portion 12 is configured to facilitate shaping the composite restoration R so that the marginal ridge generally matches a shape of a natural tooth (e.g., to have a rounded marginal ridge), i.e., without sharp bends or corners and without a tabletop structure.

Referring still to FIGS. 1-5, dental shaping strip 10 is preferably formed of a metal or plastic substrate with an abrasive surface on the shaping portion 14. Some examples of suitable metals are steel alloy, stainless steel and titanium. However, it will be apparent to those skilled in the art from this disclosure that any metallic material suitable for use in the human body can be used for the substrate without departing from the present invention. For the sake of convenience, a metal substrate is illustrated herein without the intention of limiting the instant invention to such structure. In any case, it will be apparent to those skilled in the art that any metallic or non-metallic material suitable for use in the human body can be used for the substrate without departing from the present invention.

In any case, regardless of the material used for the substrate, the material should be flexible (resilient), yet self supporting. In other words, the dental shaping strip 10 in accordance with the present invention is flexible (elastically bendable/deformable), but preferably has a pre-formed shape to which the dental shaping strip 10 returns after any elastic deformation. Some examples of preformed shapes of the dental shaping strip 10 in accordance with the present invention will be explained in more detail below with reference to FIGS. 7, 10 and 11.

Suitable abrasives for the shaping portion 14 include diamond and aluminum oxide particles. However, it will be apparent to those skilled in the art from this disclosure that any abrasive material suitable for use in the human body can be used on the shaping portion 14 without departing from the present invention. In the case of a metal substrate, the abrasive particles are preferably bonded to the metal with an adhesive, applied using electro deposition, or any other suitable conventional technique. In the case of a plastic substrate, the abrasive particles can be bonded to the plastic with an adhesive, can be molded into the plastic material, or applied using any other suitable conventional technique. While examples of abrasive particles bonded to a substrate are illustrated herein, it will be apparent to those skilled in the art from this disclosure that an abrasive or textured surface can be integrally formed in the substrate as an alternative, in other words, the metal or plastic substrate can be treated to form a textured surface thereof in order to provide the abrasive surface of the shaping portion 14. Different grits (abrasiveness) can be provided. For example, medium, fine and superfine grits can be provided on different dental shaping strips 10. Also, a gradient of grits on the same dental shaping strip 10 can be provided.

Referring now to FIGS. 2-9, the structure of the dental shaping strip 10 will now be explained in more detail. As mentioned above, the dental shaping strip 10 basically includes the base portion 12 and the shaping portion 14. Preferably, the shaping portion 14 is integrally formed with the based portion 12 as a one-piece unitary member. In the illustrated embodiment, the substrate of the base portion 12 and the shaping portion 14 is metal.

The base portion 12 has a first base surface 22 and a second base surface 24 facing in an opposite direction from the first base surface 22. The base portion 12 is preferably a thin, rectangular, plate shape member with the first base surface 22 and the second base surface 24 being parallel to each other. The base portion 12 preferably has a thickness between about 0.025 mm and about 0.050 mm. In other words, the base portion 12 preferably has a thickness between about 0.001 inches and about 0.002 inches. The first and second base surfaces 22 and 24 have prescribed longitudinal lengths $L_1$ and $L_2$, and prescribed widths $W_1$ and $W_2$ transverse to the prescribed longitudinal lengths $L_1$ and $L_2$, respectively. In the illustrated embodiment, the first and second base surfaces 22 and 24 are rectangular and the prescribed longitudinal lengths $L_1$ and $L_2$ are significantly larger than prescribed widths $W_1$ and $W_2$.

The first and second base surfaces 22 and 24 are at least partially non-abrasive. Preferably, the first and second base surfaces 22 and 24 are non-abrasive along the prescribed longitudinal lengths $L_1$ and $L_2$ and prescribed widths $W_1$ and $W_2$. Therefore, the base portion 12 can be received in the contact area C along any longitudinal position of the dental shaping strip 10 without abrading adjacent teeth or the composite restoration R. The term "at least partially non-abrasive" should be interpreted to mean at least part or at least a portion of the surface is non-abrasive. The term "non-abrasive" as used herein to describe a surface means a surface that will not abrade teeth. In addition, the term "non-abrasive" as used herein to describe a surface means the surface feels smooth to the touch of a human and preferably looks smooth to the naked eye of a human.

The shaping portion 14 is connected to a longitudinal edge of the base portion 12. In the illustrated embodiment, the shaping portion 14 has the same thickness as the base portion 12. The shaping portion 14 has a first shaping surface 32 connected to the first base surface 22, and second shaping surface 34 connected to the second base surface 24. In this embodiment, the second shaping surface 34 is preferably non-abrasive like the first and second base surfaces 22 and 24 so as not to abrade an adjacent tooth. However, at least part of the first shaping surface 32 is abrasive. In the illustrated embodiment, the shaping portion 14 has the same thickness as the base portion 12, except for the abrasive particle could make the shaping portion 14 slightly thicker. The term "at least part is abrasive" should be interpreted to mean that at least a portion of the surface is abrasive. The term "abrasive" as used herein to describe a surface means a surface that will abrade (cured) composite resin and teeth. In addition, the term "abrasive" as used herein to describe a surface means the surface feels rough to the touch of a human and preferably looks rough to the naked eye of a human. In any case, a surface referred to as an "abrasive surface" should be interpreted to have a higher coefficient of friction than a surface referred to as a non-abrasive surface.

Figure 1:
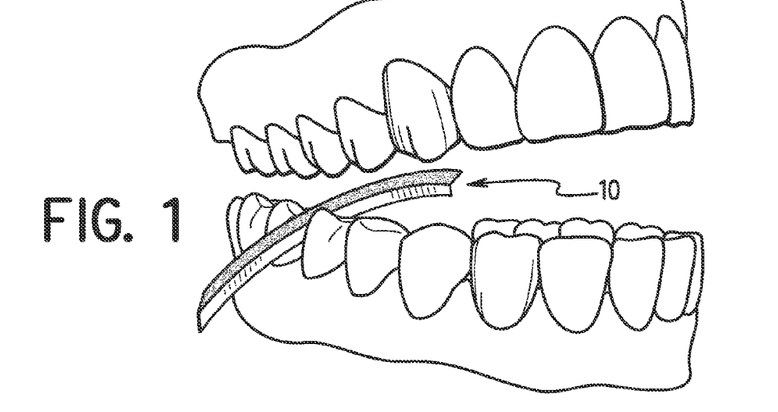
FIG. 1 is a perspective view of human dentition and a dental shaping strip in accordance with a first embodiment.
Figure 2:
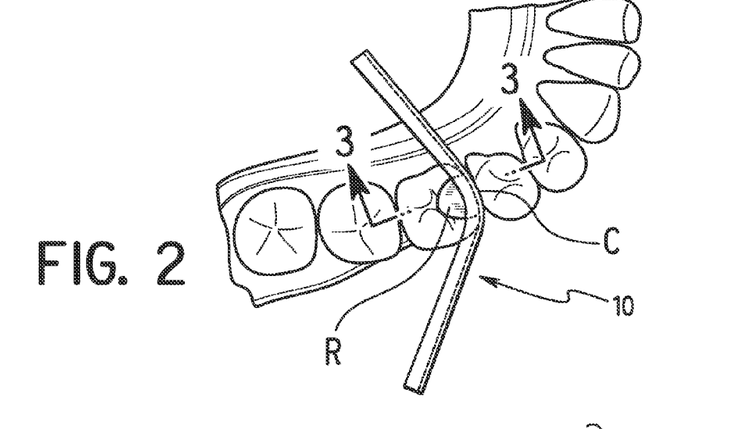
FIG. 2 is a top view of the dental shaping strip being used on an interproximal restoration of a posterior tooth of the lower dentition illustrated in FIG. 1.
Figure 3:
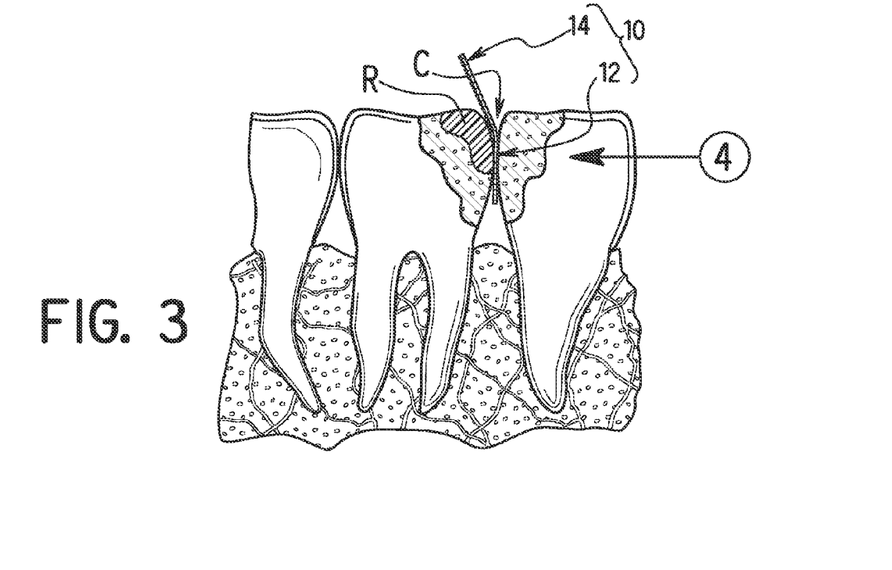
FIG. 3 is a cross-sectional view the dental shaping strip being used on the interproximal restoration of the posterior lower tooth illustrated in FIG. 2, as seen along section line 3-3 of FIG. 2.
Figures 4, 5:
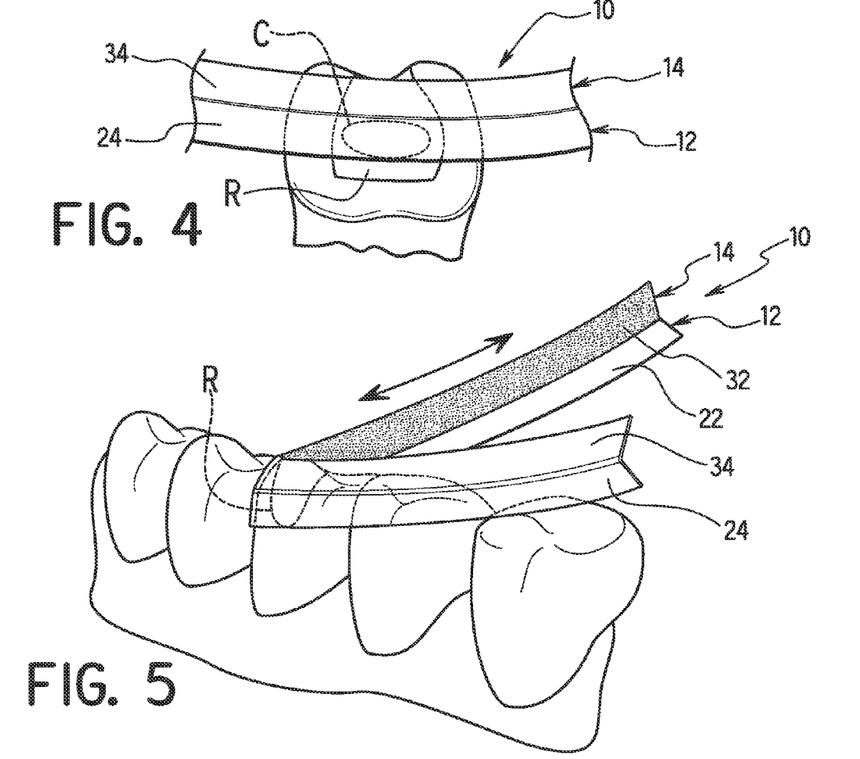
FIG. 4 is an interproximal view the dental shaping strip being used on the interproximal restoration of the posterior lower tooth illustrated in FIGS. 2-3, as seen along arrow 4 of FIG. 3.
FIG. 5 is an enlarged perspective view of the dental shaping strip being used on an opposed interproximal restoration of a posterior lower tooth illustrated in FIGS. 2-4, with movement of the dental shaping strip in order to shape the restoration illustrated with arrows.
Figure 6:
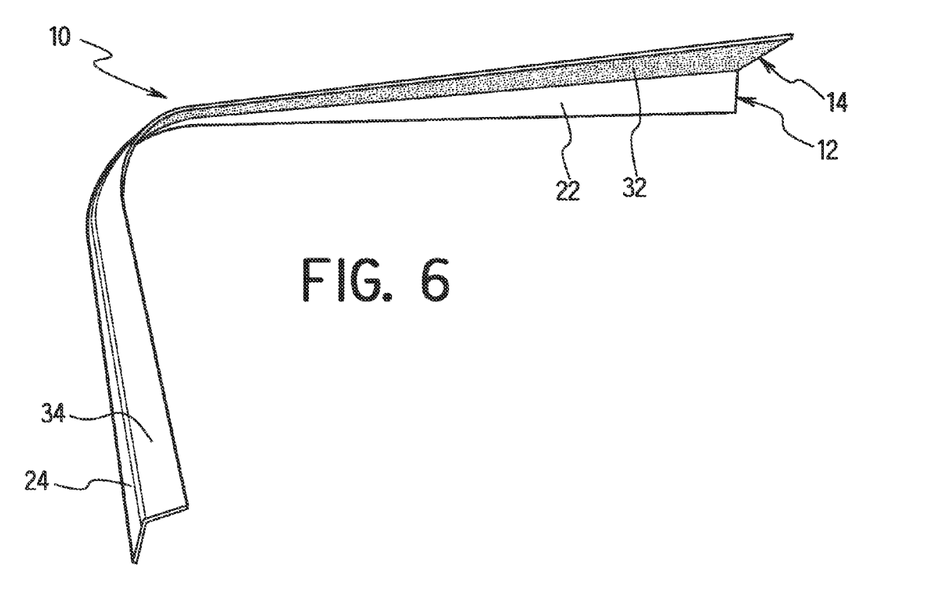
FIG. 6 is an enlarged perspective view of the dental shaping strip illustrated in FIGS. 1-5.
Figure 7:
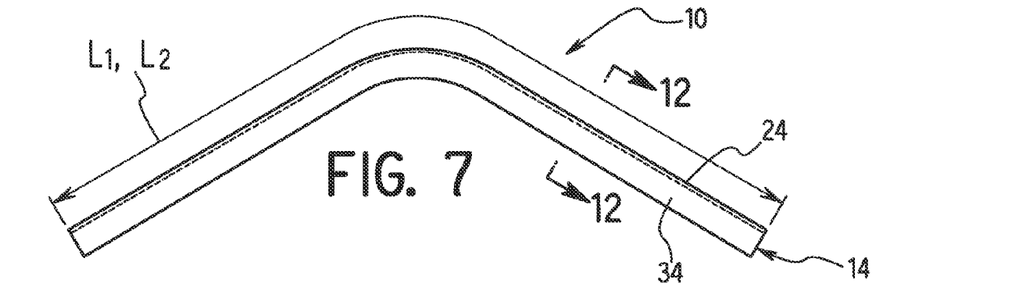
FIG. 7 is a top plan view of the dental shaping strip illustrated in FIG. 6.
Figure 8:
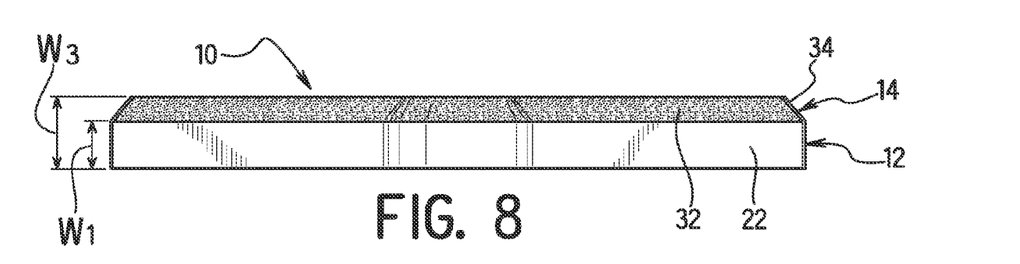
FIG. 8 is an abrasive side elevational view of the dental shaping strip illustrated in FIGS. 6-7.
Figure 9:
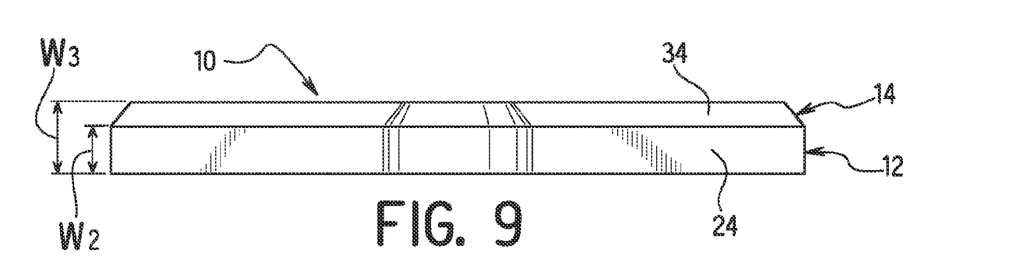
FIG. 9 is an opposite side elevational view of the dental shaping strip illustrated in FIGS. 6-8.
Figure 10:
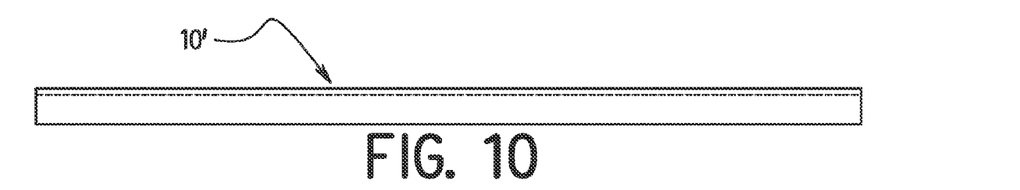
FIG. 10 is a top plan view of a linear dental shaping strip in accordance with a first modification of the first embodiment.
Figure 11:
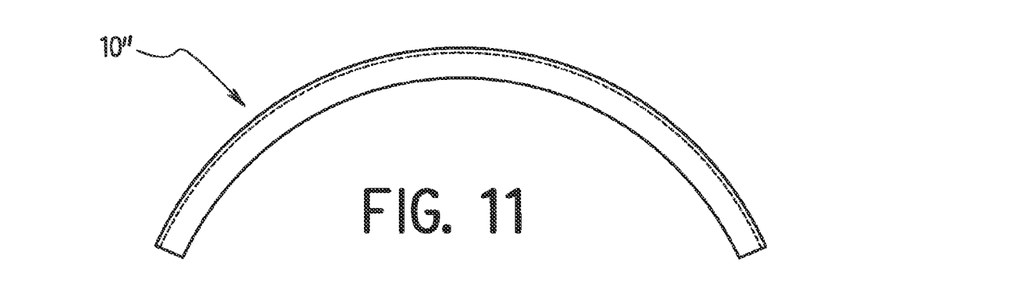
FIG. 11 is a top plan view of a curved dental shaping strip in accordance with a second modification of the first embodiment.

Referring now to FIGS. 7-11, the overall longitudinal shape of the dental shaping strip 10 will now be described in more detail. In FIGS. 7-9, the dental shaping strip 10 has linear ends and a curved center portion. Therefore, the dental shaping strip 10 is at least partially linear along a longitudinal direction of the dental shaping strip 10, and at least partially curved along a longitudinal direction of the dental shaping strip 10. However, the dental shaping strip can have other longitudinal configurations without departing from the invention. For example, a modified dental shaping strip 10' is illustrated in FIG. 10, which has a longitudinally linear configuration, and a modified dental shaping strip 10" is illustrated in FIG. 11, which has a longitudinally curved configuration. Regardless of the longitudinal shape of the dental shaping strip 10, 10' and/or 10", the dental shaping strip 10, 10' and/or 10" preferably has a uniform cross-sectional profile along the entire longitudinal length thereof. The dental shaping strips 10' and 10" are identical to the dental shaping strip 10, except for the longitudinal shapes thereof. Therefore, it will be apparent to those skilled in the art from this disclosure that the descriptions and illustrations of the dental shaping strip 10 also apply to the dental shaping strips 10' and 10", except as explained and illustrated herein. Accordingly, for the sake of brevity, only the dental shaping strip 10 will now be explained in further detail. The illustrated shapes can be achieved by using conventional rollers and/or sheet metal forming machines to obtain shapes of the dental shaping members 10, 10' and/or 10".

Figure 12:
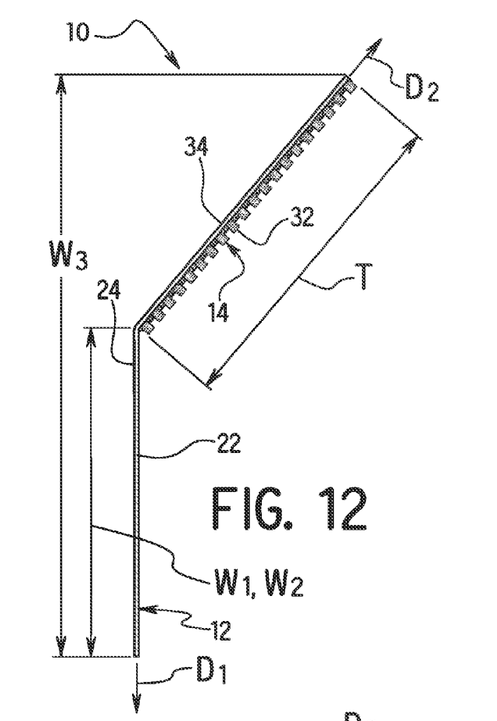
FIG. 12 is an enlarged view of a first cross-sectional profile of the dental shaping strip illustrated in FIGS. 2-11 (applicable to the first embodiment and the first and second modifications), as seen along section line 12-12 of FIG. 7.

Referring now to FIGS. 2-9 and 12-15, the arrangement of the shaping portion 14 relative to the base portion 12 will now be explained in more detail. In this embodiment, the first shaping surface 32 and the first base surface 22 preferably diverge from each other as the first base surface 22 and the first shaping surface 32 approach longitudinal free edges of the dental shaping strip 10. In this embodiment, the dental shaping strip 10 has a transverse cross-sectional profile as shown in any one of FIGS. 12-15. In FIGS. 2-11, the cross-sectional profile of FIG. 12 is used for the sake of convenience. In any case, the first base surface 22 diverges in a first linear direction $D_1$ from the first shaping surface 32.

Figure 13:
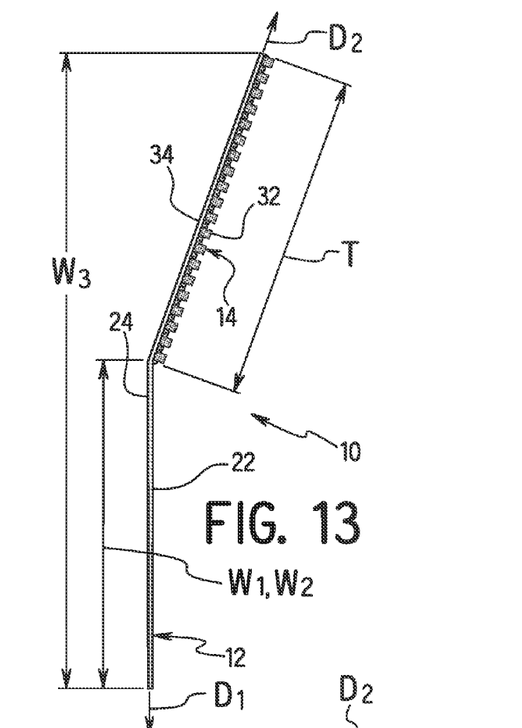
FIG. 13 is an enlarged view of a second cross-sectional profile of the dental shaping strip illustrated in FIGS. 2-11 (applicable to the first embodiment and the first and second modifications), as seen along section line 12-12 of FIG. 7.
Figure 14:
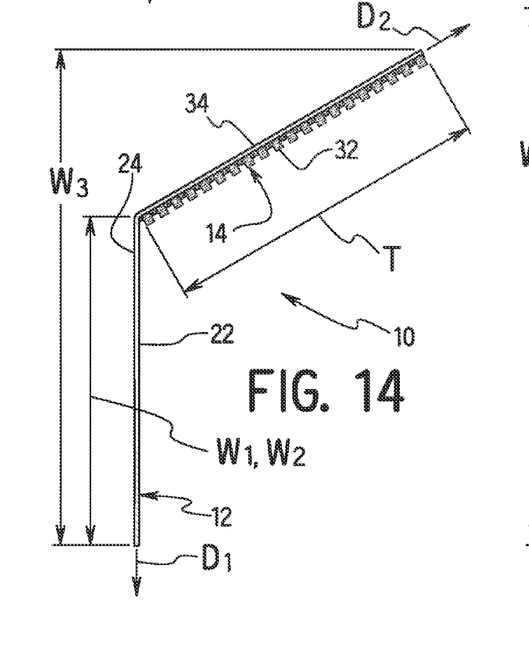
FIG. 14 is an enlarged view of a third cross-sectional profile of the dental shaping strip illustrated in FIGS. 2-11 (applicable to the first embodiment and the first and second modifications), as seen along section line 12-12 of FIG. 7.

In the cross-sectional profiles illustrated in FIGS. 12-14, the dental shaping strip 10 has a fold or bend formed between the base portion 12 and the shaping portion 14. The first shaping surface 32 diverges in a second linear direction $D_2$ from the first base surface 22 in the transverse cross-sectional profile such that the first linear direction $D_1$ is inclined relative to the second linear direction $D_2$. Preferably, the second direction $D_2$ is inclined between about 20 degrees and about 60 degrees relative to the first direction $D_1$ in the transverse cross-sectional profile. FIG. 12 illustrates an angle of about 40 degrees, FIG. 13 illustrates an angle of about 20 degrees, and FIG. 14 illustrates an angle of about 60 degrees. In the illustrated cross-sectional profiles of FIGS. 12-13, the prescribed width $W_1$ of the first base surface measured along the first linear direction $D_1$ is approximately equal to a transverse width T of the first shaping surface measured along the second linear direction $D_2$. While it will be apparent to those skilled in the art from this disclosure that other angles could be utilized, FIGS. 12-14 illustrate three preferred examples.

Figure 15:
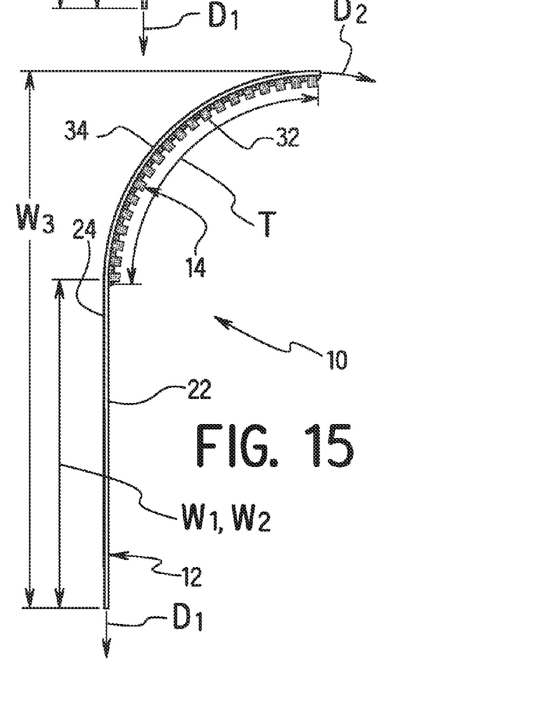
FIG. 15 is an enlarged view of a fourth cross-sectional profile applicable to the dental shaping strip illustrated in FIGS. 2-11 (applicable to the first embodiment and the first and second modifications), as seen along section line 12-12 of FIG. 7.

On the other hand, in the cross-sectional profile illustrated in FIG. 15, the first shaping surface 32 diverges in a second curved direction $D_2$ from the first base surface 22 in the transverse cross-sectional profile. As seen in FIG. 15, the second curved direction $D_2$ is concavely curved on a first shaping side of the dental shaping strip 10. Like the profiles illustrated in FIGS. 12-14, in the profile of FIG. 15, the prescribed width $W_1$ of the first base surface measured along the first linear direction $D_1$ is approximately equal to a transverse width T of the first shaping surface measured along the second curved direction $D_2$.

In all of the profiles of FIGS. 12-15, because the shaping portion 14 diverges from the base portion 12, the prescribed widths $W_1$ and $W_2$ of the first and second base surfaces 22 and 24 are at least about 50% of an overall transverse width $W_3$ of the dental shaping strip as measured along the first and second base surfaces 22 and 24. In the illustrated profiles, prescribed widths $W_1$ and $W_2$ of the first and second base surfaces 22 and 24 are between 51% and about 66.7% of an overall transverse width $W_3$ of the dental shaping strip 10 as measured along the first and second base surfaces 22 and 24. It will be apparent to those skilled in the art from this disclosure that the shaping portion 14 can be made longer than the base portion 12 due to the diverging arrangement of the shaping portion 14, which would reduce the above percentage. However, the base portion 12 should be sufficiently wide to fit in the contact area C. In other words, prescribed widths $W_1$ and $W_2$ of the first and second base surfaces 22 and 24 should preferably be at least 33% of an overall transverse width $W_3$ of the dental shaping strip 10. As one alternative example, prescribed widths $W_1$ and $W_2$ of the first and second base surfaces 22 and 24 are about 50% of an overall transverse width $W_3$ of the dental shaping strip 10.

The dental shaping strip 10 is preferably between 120 mm and 200 mm long and between 2.5 mm and 6 mm wide. However, it will be apparent to those skilled in the art from this disclosure that these dimensions can be adjusted as needed and/or desired. In the illustrated embodiment, the width dimensions vary depending on the profile selected (e.g. of FIGS. 12-15 for example).

Use of the dental shaping strip 10 will now be explained in more detail. In the illustrated embodiment, abrasive is preferably applied to only one half longitudinally on the first side. Preferably, the other half of the first side and the entire second side is smooth (non-abrasive) or safe (i.e., will not abrade the teeth or restoration R). After placing a new interproximal composite restoration, the interproximal composite restoration R is cured. Then the dental shaping strip is used to shape the cured composite restoration R. The dental shaping strip 10 is held in tension between thumb and forefinger of each hand of the dentist and (the base portion 12) is inserted between the interproximal contacts (i.e., to abut the contact area of the newly placed composite restoration R as well as the adjacent tooth). The dental shaping strip 10 can then be moved back and forth to shape the occlusal embrasure (marginal ridge) with the shaping portion 14, which diverges from the base portion 12 to firm a concave first side of the dental shaping strip 10. The strip is gripped in a conventional fashion with two hands to insert it, to move it, and to remove it from the contact area C. The concave abrasive surface is touching the occlusal embrasures, which become shaped in the desired "V" shaped form as the shaping strip 10 is drawn back and forth. Any back and forth movement of the dental shaping strip 10 is guided by the contact area C and the base portion 12 interposed in the contact area C, but does not diminish the contact's tightness.

Second Embodiment

Figures 16, 17, 18:
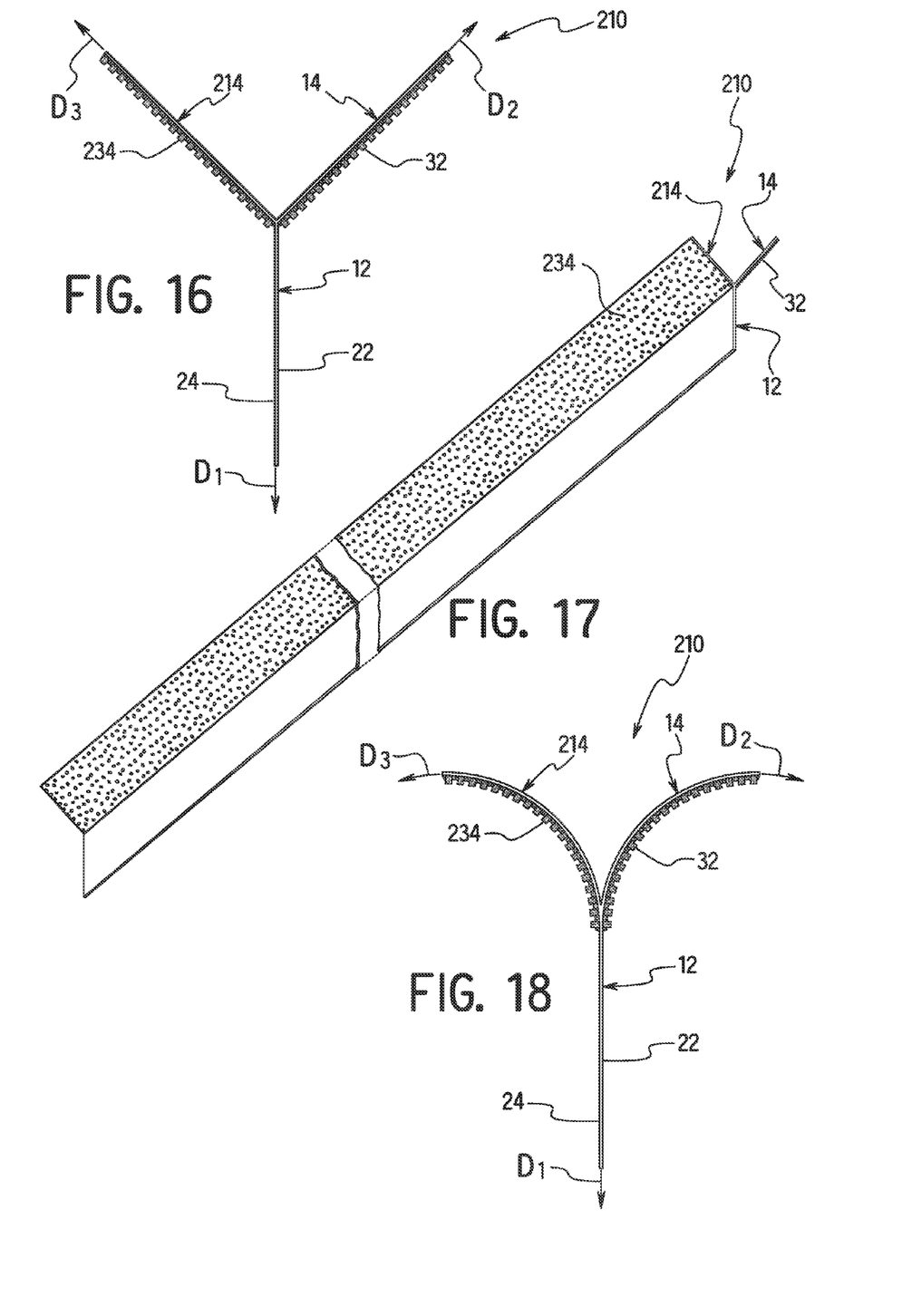
FIG. 16 is an enlarged view of a fifth cross-sectional profile applicable to the linear dental shaping strip illustrated in FIG. 10 in accordance with a second embodiment.
FIG. 17 is a perspective view of a dental shaping strip incorporating the fifth cross-sectional profile of FIG. 16 into the linear dental shaping strip of FIG. 10 in accordance with the second embodiment.
FIG. 18 is an enlarged view of a sixth cross-sectional profile applicable to the linear dental shaping strip illustrated in FIGS. 10 and 17 in accordance with the second embodiment.

Referring now to FIGS. 16-18, a dental shaping strip 210 in accordance with a second embodiment will now be explained. In view of the similarity between the first and second embodiments, the parts of the second embodiment that are identical to the parts of the first embodiment will be given the same reference numerals as the parts of the first embodiment. Moreover, the descriptions of the parts of the second embodiment that are identical to the parts of the first embodiment may be omitted for the sake of brevity. In other words, the descriptions and illustrations of the first embodiment also apply to this second embodiment, except as explained and illustrated herein. Furthermore, it will be apparent from this disclosure that parts of this embodiment that are identical or functionally identical will be given the same reference numerals as the first embodiment but with "200" added thereto.

The dental shaping strip 210 is identical to the shaping strip 10 of the first embodiment, except the dental shaping strip 210 includes an additional shaping portion 214 in addition to the shaping portion 14 of the first embodiment to form a substantially "Y" shaped configuration. In view of the similarities between this second embodiment and the first embodiment, it will be apparent to those skilled in the art from this disclosure that the descriptions and illustrations of the first embodiment (including the profiles illustrated in FIGS. 12-14) also apply to this second embodiment, except as explained. and illustrated herein. On the other hand, in this second embodiment the dental shaping strip 210 is preferably longitudinally linear (i.e., does not have a partially curved or fully curved longitudinal configuration like the dental shaping strips 10 and 10" of the first embodiment.

The dental shaping strip 210 basically includes a base portion 12, a shaping portion 14 and an additional shaping portion 214. The shaping portion 214 is preferably a mirror image of the shaping portion 14 of the first embodiment. Thus, the descriptions and illustrations of the shaping portion 14 also apply to the shaping portion 214. Thus, the shaping portion 214 includes a second shaping surface 234, with the second shaping surface 234 being at least partially abrasive. The second shaping surface 234 and the second base surface 24 diverge from each other as the second base surface 24 and the second shaping surface 234 approach longitudinal free edges of the dental shaping strip 210.

One example profile is illustrated in FIG. 16, which generally corresponds to the profile illustrated in FIG. 12. Thus, the dental shaping strip 210 has a transverse cross-sectional profile in which the first and second base surfaces 22 and 24 diverge in a first linear direction $D_1$ from the first and second shaping surfaces 34 and 234, respectively. Therefore, the first shaping surface 34 diverges in a second linear direction $D_2$ from the first base surface 22 in the transverse cross-sectional profile such that the first linear direction $D_1$ is inclined relative to the second linear direction, and the second shaping surface 234 diverges in a third linear direction $D_3$ from the second base surface 24 in the transverse cross-sectional profile such that the first linear direction $D_1$ is inclined relative to the third linear direction $D_3$.

Another example profile is illustrated in FIG. 18, which generally corresponds to the profile illustrated in FIG. 15. Thus, the dental shaping strip 210 may alternatively have the first shaping surface 32 diverging in a second curved direction $D_2$ from the first base surface 22 in the transverse cross-sectional profile, and the second shaping surface 234 diverging in a third curved direction $D_3$ from the second base surface 24 in the transverse cross-sectional profile.

This second embodiment can be used to shape a pair of interproximal composite restorations located next to each other at the same time. This is why the linear configuration is used. In view of the similarities between this second embodiment and the first embodiment, this second embodiment will not be explained in further detail herein.

Third Embodiment

Referring now to FIG. 19-25, a dental shaping strip 310 in accordance with a third embodiment will now be explained. In view of the similarity between the first and third embodiments, the parts of the third embodiment that are identical to the parts of the first embodiment will be given the same reference numerals as the parts of the first embodiment. Moreover, the descriptions of the parts of the third embodiment that are identical to the parts of the first embodiment may be omitted for the sake of brevity. In other words, the descriptions and illustrations of the first embodiment also apply to this third embodiment, except as explained and illustrated herein. Furthermore, it will be apparent from this disclosure that parts of this embodiment that are identical or functionally identical will be given the same reference numerals as the first embodiment but with "300" added thereto.

The dental shaping strip 310 is identical to the shaping strip 10 of the first embodiment, i.e., the cross-section profile illustrated in FIG. 14, except the dental shaping strip 310 includes a holding portion 16 extending from the shaping portion 14. The added holding portion 16 is above the shaping portion 14 with the (abrasive) first shaping surface 32 when used on lower dentition and below the shaping portion 14 with the (abrasive) first shaping surface 32 when used on upper dentition. The added holding portion 16 facilitates holding the dental shaping strip 310 in a rigid manor with a hemostat H or an equivalent tool. This holding portion 16 also acts a rigid stiffener and holder, which allows the dental shaping strip 310 to be inserted easily, and allows force to be applied to the first abrasive surface 32 of the shaping portion 14 in order to push the shaping portion 14 against the tooth restoration R with the holding tool.

Figure 21:
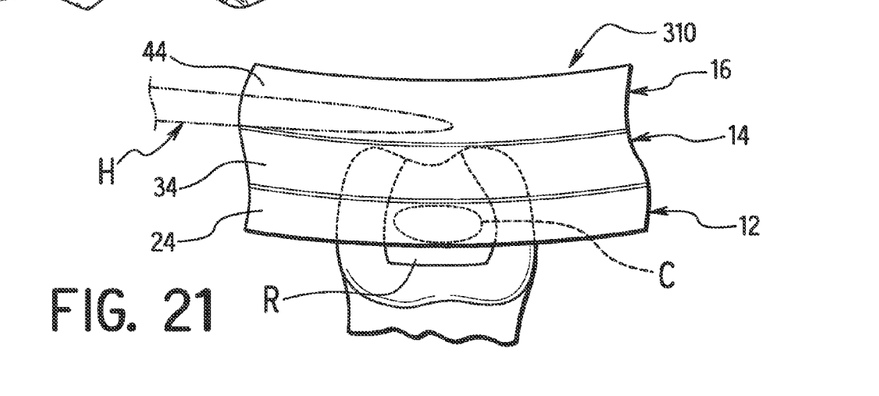
FIG. 21 is an interproximal view the dental shaping strip being used on the interproximal restoration of the posterior lower tooth illustrated in FIGS. 19-20, as seen along arrow 21 of FIG. 20.
Figure 22:
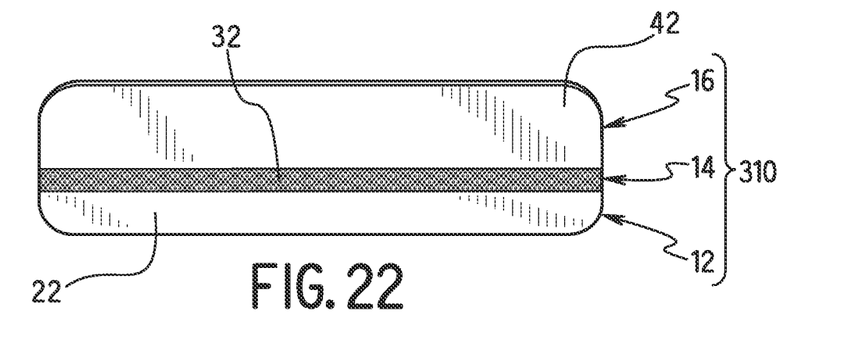
FIG. 22 is an abrasive side elevational view of the dental shaping strip illustrated in FIGS. 19-21.
Figure 23:
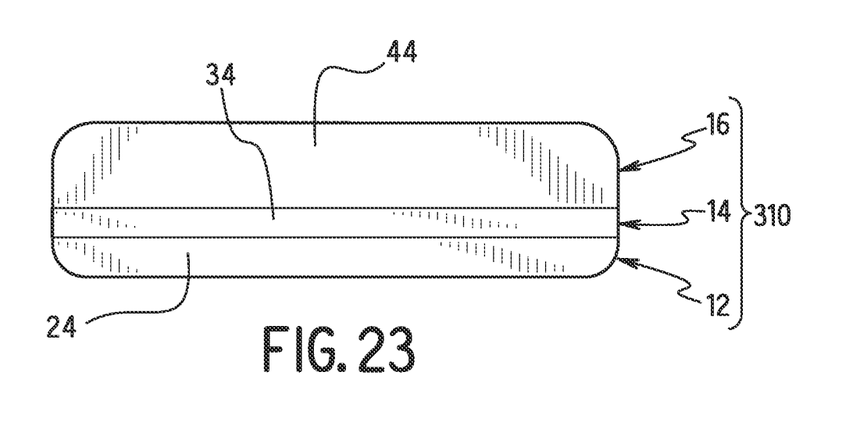
FIG. 23 is an opposite side elevational view of the dental shaping strip illustrated in FIGS. 19-221.
Figure 24:
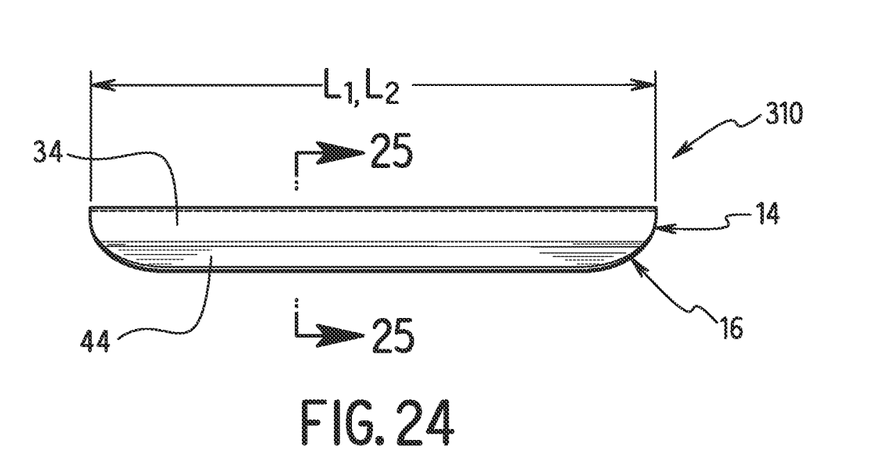
FIG. 24 is a top plan view of the dental shaping strip illustrated in FIGS. 22-23.

In addition, because the dental shaping strip 310 can be held with a hemostat or the like, the length of the dental shaping strip 310 can be reduced because it is not necessary for the practitioner to hold longitudinal ends of the shaping strip 310 during use. This reduced length can make the dental shaping strip 310 more easily maneuvered in and near the patient's mouth. The length is preferably between about 10 millimeters and about 40 millimeters. More preferably, the length is between about 15 millimeters and about 30 millimeters. In the illustrated embodiment the length is about 20 millimeters. FIGS. 19 and 22-24 illustrate a longer length for the purpose of illustration. In any case, the first and second base surfaces 22 and 24 of the base portion 12 have prescribed longitudinal lengths $L_1$ and $L_2$, which also correspond to the lengths of the shaping portion 14 and the holding portion 16 (i.e., overall length). Furthermore, in this embodiment, the base portion 12 has a width slightly smaller than in the first embodiment. In any case, the width of the base portion 12 is (preferably wide enough to fill the contact area C between adjacent teeth like the first embodiment, as seen in FIG. 21. Finally, the dental shaping strip 310 has a linear configuration like the modified dental shaping strip 10 illustrated in FIG. 10.

The dental shaping strip 310 is illustrated as a metal shaping strip like the preceding embodiments. Due to the illustrated metal construction, the holding portion 16 can be bent relative to the shaping portion 14. This bending can take place in a manufacturing facility or in a practitioner's office. In the case of a plastic dental shaping strip 310, the holding portion 16 with the desired bend/angle can be achieved with an attached plastic injected part integral to the dental shaping strip 310, since the plastic may not be plastically deformable after constructing the dental shaping strip 310 in the factory.

Bending is not required. In such a case, the holding portion 16 extends linearly from the free end of the shaping portion 14 along the direction $D_2$, as seen in phantom lines FIG. 25. Moreover, it is also possible to have the holding portion 16 bent more than is illustrated, e.g. 60 degrees relative to the direction $D_2$ as shown in phantom lines in FIG. 25. In fact, the holding portion may even be bent in an opposite direction, e.g., in the case of the profile illustrated in FIG. 13. In the illustrated embodiment, the holding portion 16 is inclined relative to the extending direction $D_2$ of the shaping portion about 40 degrees, and about 20 degrees relative to the direction $D_1$.

Figure 25:
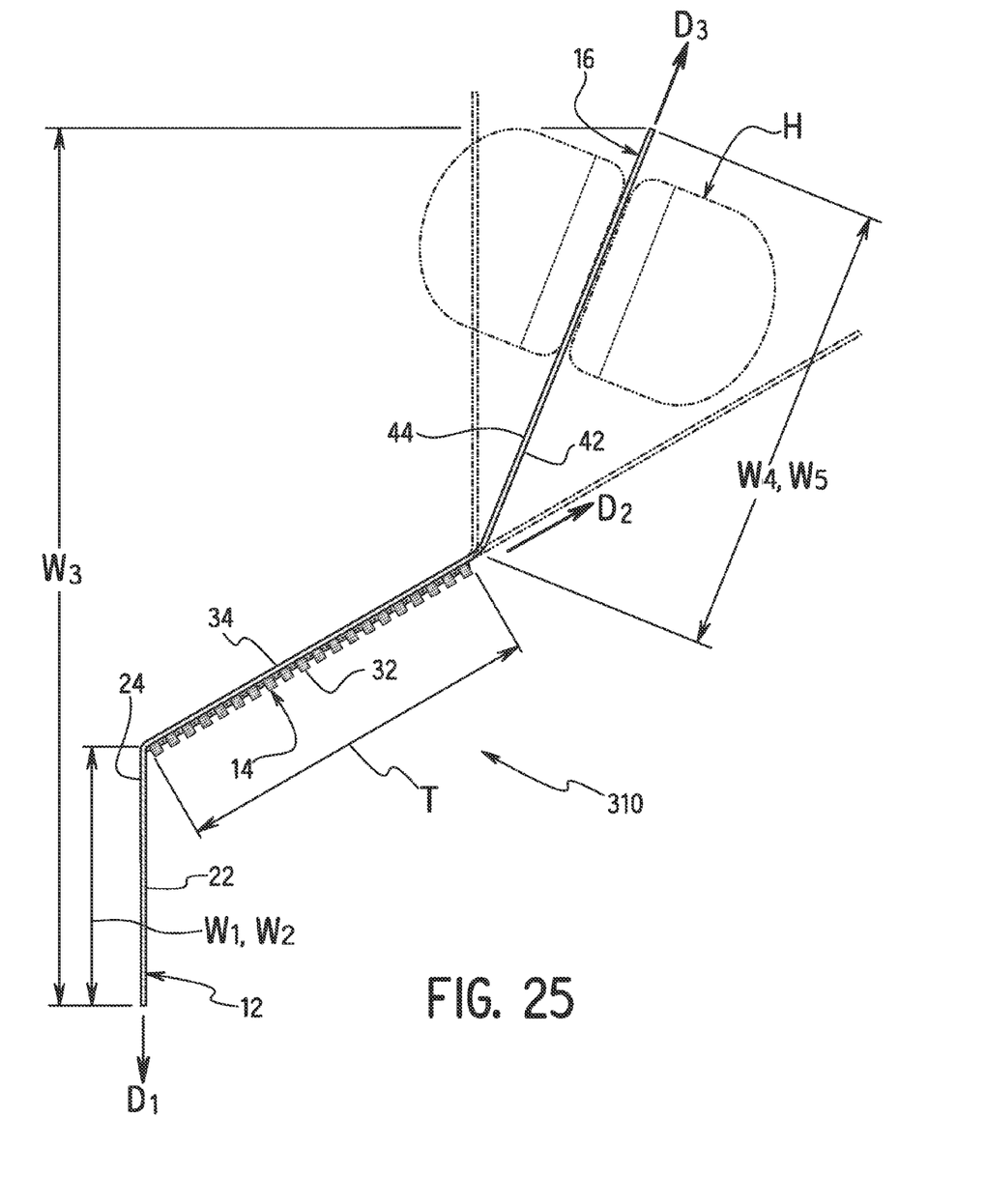
FIG. 25 is an cross-sectional view of the dental shaping strip illustrated in FIGS. 19-24 (with a cross-sectional profile similar to FIG. 14 of the first embodiment), as seen along section line 25-25 of FIG. 24.
Figure 26:
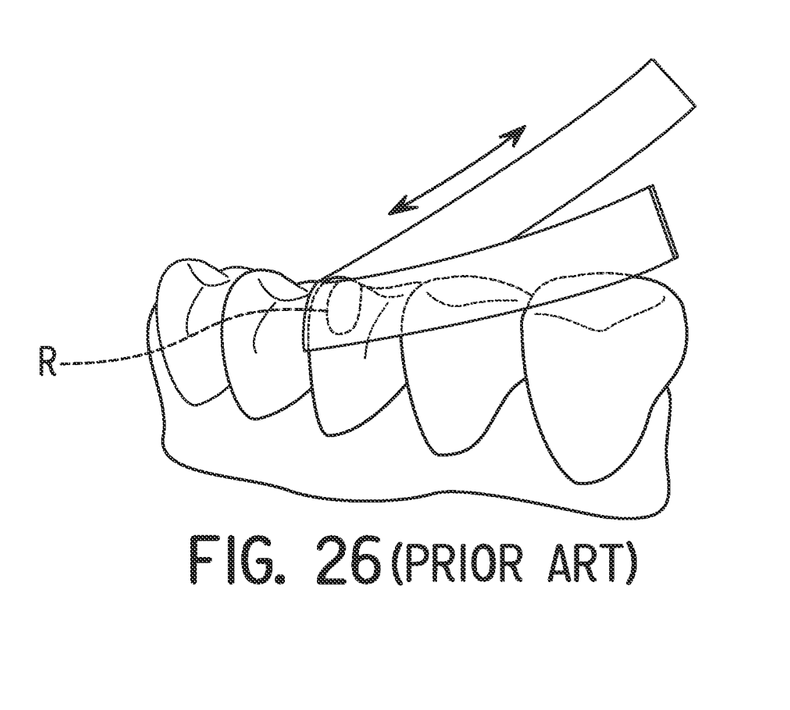
FIG. 26 is an outside perspective view of a conventional dental shaping strip being used on an interproximal restoration of a posterior lower tooth.
Figure 27:
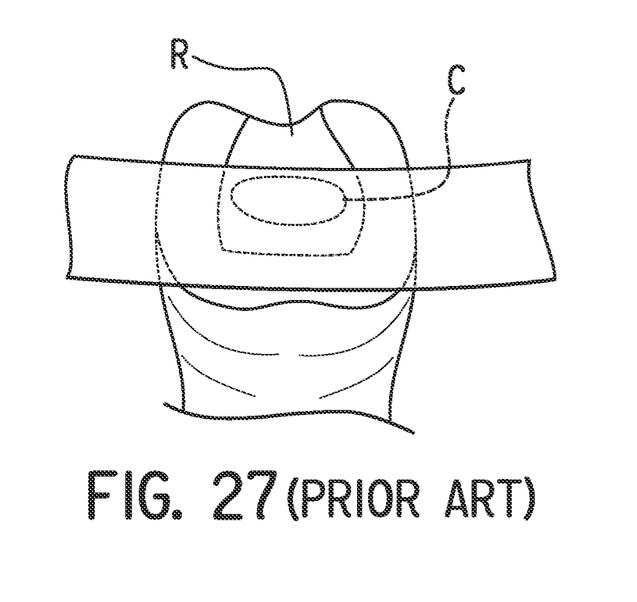
FIG. 27 is an interproximal view the conventional dental shaping strip being used on the interproximal restoration of the posterior lower tooth illustrated in 26.

Of course, depending on which profile for the shaping portion 14 is desired, i.e., of FIG. 12, FIG. 13, FIG. 14 or FIG. 15, a different angle relative to the direction $D_2$ may be selected in order to have the holding portion 16 in the position desired by the practitioner. However, the holding portion 16 is preferably bent relative to the shaping portion 14 to form a generally zigzagged or stretched Z-shaped configuration dental shaping strip 310 as best shown in FIG. 25, with the exact angle depending on which angle (profile) for the shaping portion 14 relative to the base portion 12 is selected. Preferably, the angle of the holding portion 16 relative to the direction $D_2$ at the end of the shaping portion 14 is between 0 degrees and 60 degrees in either direction but preferably in a direction which results in a zigzagged configuration.

The holding portion 16 includes a first holding surface 42 extending from the first shaping surface 32 and a second holding surface 44 extending from the second shaping surface 34. The first and second holding surfaces 42 and 44 face in opposite directions. Preferably, the holding portion 16 has a thickness identical to the thickness of the base portion 12 and the shaping portion 14, discussed above with reference to the first embodiment. In the illustrated embodiment, the first and second holding surfaces 42 and 44 are non-abrasive surfaces. However it will be apparent to those skilled in the art from this disclosure that the first and second holding surfaces 42 and 44 could be textured and/or abrasive surfaces to facilitate holding the dental shaping strip 310 with the hemostat H or an equivalent tool.

The holding portion 16 is preferably a thin, rectangular, plate shape member with the first holding surface 42 and the second holding surface 44 being parallel to each other. The holding portion 16 extends in a third direction $D_3$ from the shaping portion 14. The third direction $D_3$ is preferably a linear direction. Preferably, the free corners of the holding portion 16 are rounded. In addition, in this embodiment, the free corners of the base portion 12 are rounded. The first and second holding surfaces 42 and 44 have prescribed widths $W_4$ and $W_5$ transverse to the prescribed longitudinal length.

In the illustrated embodiment, the prescribed widths $W_4$ and $W_5$ are larger than widths $W_1$ and $W_2$ of the base portion 112 and larger than the transverse width T of the shaping portion 14. In the illustrated embodiment, the prescribed widths $W_4$ and $W_5$ are preferably between about 5 millimeters and about 7 millimeters, while the widths $W_1$ and $W_2$ are preferably about 3 millimeters. In the illustrated embodiment, the transverse width T is preferably between about 4 millimeters and about 5 millimeters. Thus, the prescribed widths $W_4$ and $W_5$ are preferably larger than the transverse width T, with the transverse width T preferably being larger than the widths $W_1$ and $W_2$.

The holding portion 16 is connected to a longitudinal edge of the shaping portion 14 remote from the base portion 12. In the cross-sectional profile illustrated in FIGS. 19-25, the dental shaping strip 310 has a fold or bend formed between the base portion 12 and the shaping portion 14 and between the shaping portion 14 and the holding portion 16. In this embodiment, because the base portion 12 is narrower and because the holding portion 16 is present, the prescribed widths $W_1$ and $W_2$ of the first and second base surfaces 22 and 24 are about 50% or less than an overall transverse width $W_3$ of the dental shaping strip 310, e.g., about 25-30% of an overall width of the dental shaping strip 310. However, depending on the profile selected for the shaping portion 14 and angle of the holding portion 16, the relative size of the prescribed widths $W_1$ and $W_2$ could be smaller than 25-30%, i.e., less than 30%. Due to the numerous possible configurations, the relative sizes will not be discussed and/or illustrated herein with respect to every possibility. However, it will be apparent to those skilled in the art from this disclosure that the prescribed widths $W_1$ and $W_2$ as compared to the overall width $W_3$ of the dental shaping strip 310 can be extrapolated from the profiles of FIGS. 12-15 and from the variable angle attic holding portion 16 shown in FIG. 25.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Also as used herein to describe the above embodiment(s), the following directional terms "proximal", "interproximal", "posterior", "longitudinal" and "transverse" as well as any other similar directional terms refer to those directions of the dental shaping strip or relative to the human body in which the dental shaping strip is used. Accordingly, these terms, as utilized to describe the present invention should be interpreted relative to the dental shaping strip or relative to the human body in which the dental shaping strip is used.

The terms of degree such as "substantially", "about" and "approximately" as used herein mean a reasonable amount of deviation of the modified term such that the end result is not significantly changed.

While only selected embodiments have been chosen to illustrate the present invention, it will be apparent to those skilled in the art from this disclosure that various changes and modifications can be made herein without departing from the scope of the invention as defined in the appended claims. For example, the size, shape, location or orientation of the various components can be changed as needed and/or desired, corresponding to the variation of sizes of teeth in nature. Components that are shown directly connected or contacting each other can have intermediate structures disposed between them. The functions of one element can be performed by two, and vice versa. The structures and functions of one embodiment can be adopted in another embodiment. It is not necessary for all advantages to be present in a particular embodiment at the same time. Every feature which is unique from the prior art, alone or in combination with other features, also should be considered a separate description of further inventions by the applicant, including the structural and/or functional concepts embodied by such feature(s). Thus, the foregoing descriptions of the embodiments according to the present invention are provided for illustration only, and not for the purpose of limiting the invention as defined by the appended claims and their equivalents.

What is claimed is:

1. A dental shaping strip comprising:
a base portion having a first base surface and a second base surface facing in an opposite direction from the first base surface, the first and second base surfaces having prescribed longitudinal lengths and prescribed widths transverse to the prescribed longitudinal lengths, the prescribed longitudinal lengths being larger than the prescribed transverse widths;
a shaping portion connected to a longitudinal edge of the base portion, the shaping portion having a first shaping surface connected to the first base surface on a common side of the dental shaping strip, with at least part of the first shaping surface being abrasive; and
a holding portion extending from a longitudinal edge of the shaping portion spaced from the base portion, the holding portion having a first holding surface extending from the first shaping surface on the common side of the dental shaping strip,
the first and second base surfaces being at least partially non-abrasive,
the first shaping surface and the first base surface diverging from each other as the first shaping surface extends away from the longitudinal free edge of the base portion of the dental shaping strip, as viewed in transverse cross-section along a longitudinal direction of the dental shaping strip, such that the first shaping surface is obtuse relative to the first base surface, and
the holding portion and the shaping portion diverging from each other as the holding portion extends away from the longitudinal edge of the shaping portion, as viewed in transverse cross-section along the longitudinal direction of the dental shaping strip, such that the first shaping surface is reflex angled relative to the first holding surface.

2. The dental shaping strip according to claim 1, wherein the dental shaping strip has a transverse cross-sectional profile in which the first base surface diverges in a first linear direction from the first shaping surface.

3. The dental shaping strip according to claim 2, wherein the first shaping surface diverges in a second linear direction from the first base surface in the transverse cross-sectional profile such that the first linear direction is inclined relative to the second linear direction.

4. The dental shaping strip according to claim 3, wherein the second linear direction is inclined between about 20 degrees and about 60 degrees relative to the first linear direction in the transverse cross-sectional profile.

5. The dental shaping strip according to claim 3, wherein the prescribed width of the first base surface measured along the first linear direction is approximately equal to or less than a transverse width of the first shaping surface measured along the second linear direction.

6. A dental shaping strip comprising:
a base portion having a first base surface and a second base surface facing in an opposite direction from the first base surface, the first and second base surfaces having prescribed longitudinal lengths and prescribed widths transverse to the prescribed longitudinal lengths, the prescribed longitudinal lengths being larger than the prescribed transverse widths;
a shaping portion connected to a longitudinal edge of the base portion, the shaping portion having a first shaping surface connected to the first base surface on a common side of the dental shaping strip, with at least part of the first shaping surface being abrasive; and
a holding portion extending from a longitudinal edge of the shaping portion spaced from the base portion, the holding portion having a first holding surface extending from the first shaping surface on the common side of the dental shaping strip,
the first and second base surfaces being at least partially non-abrasive,
the first shaping surface and the base surface diverging from each other as the first shaping surface extends away from the longitudinal free edge of the base portion of the dental shaping strip, as viewed in transverse cross-section along a longitudinal direction of the dental shaping strip, the first shaping surface diverging in a curved direction from the first base surface, and the curved direction being concavely curved on the common side of the dental shaping strip, as viewed in transverse cross-section along a longitudinal direction of the dental shaping strip, and the holding portion and the shaping portion diverging from each other as the holding portion extends away from the longitudinal edge of the shaping portion, as viewed in transverse cross-section along the longitudinal direction of the dental shaping strip, such that the first holding surface is reflex angled relative to a portion of the first shaping surface at the longitudinal edge of the shaping portion.

7. The dental shaping strip according to claim 6, wherein the prescribed width of the first base surface measured along the first linear direction is approximately equal to or less than a transverse width of the first shaping surface measured along the second curved direction.

8. The dental shaping strip according to claim 1, wherein the first and second base surfaces of the base portion being non-abrasive along the prescribed longitudinal lengths and prescribed widths thereof.

9. The dental shaping strip according to claim 1, wherein the dental shaping strip is at least partially linear along a longitudinal direction of the dental shaping strip.

10. The dental shaping strip according to claim 1, wherein the dental shaping strip is at least partially curved along a longitudinal direction of the dental shaping strip.

* * * * *